(12) United States Patent
Palmer, III et al.

(10) Patent No.: US 11,925,792 B2
(45) Date of Patent: Mar. 12, 2024

(54) APPARATUS FOR DESTROYING SHARP OBJECTS AND METHOD OF USE

(71) Applicant: RedHawk Medical Products & Services, LLC, Lafayette, LA (US)

(72) Inventors: James Palmer, III, Lafayette, LA (US); Nolan J. Edwards, II, Lafayette, LA (US)

(*) Notice: Subject to any disclaimer, the term of this patent is extended or adjusted under 35 U.S.C. 154(b) by 675 days.

(21) Appl. No.: 16/918,942

(22) Filed: Jul. 1, 2020

(65) Prior Publication Data
US 2021/0001056 A1     Jan. 7, 2021

Related U.S. Application Data

(60) Provisional application No. 62/942,041, filed on Nov. 29, 2019, provisional application No. 62/869,390, filed on Jul. 1, 2019.

(51) Int. Cl.
| | | |
|---|---|---|
| *A61M 5/32* | (2006.01) | |
| *A61B 50/36* | (2016.01) | |
| *H05B 3/02* | (2006.01) | |
| *H05B 3/03* | (2006.01) | |
| *H05B 3/12* | (2006.01) | |

(52) U.S. Cl.
CPC ......... *A61M 5/3278* (2013.01); *A61B 50/362* (2016.02); *H05B 3/03* (2013.01); *H05B 3/12* (2013.01); *A61B 2050/364* (2016.02); *A61M 2005/3283* (2013.01)

(58) Field of Classification Search
CPC ........... A61B 2050/364; A61B 50/362; A61M 2005/3283; A61M 5/3278; H05B 3/03; H05B 3/12; H05B 3/0004
See application file for complete search history.

(56) References Cited

U.S. PATENT DOCUMENTS

| | | | | |
|---|---|---|---|---|
| 3,842,724 A | * | 10/1974 | Korr | H05B 3/0004 99/332 |
| 5,391,849 A | * | 2/1995 | Furuya | A61L 9/122 219/68 |
| 5,710,404 A | * | 1/1998 | Descent | A61L 11/00 219/68 |
| 2002/0074315 A1 | * | 6/2002 | Decaire | A61M 5/3278 219/69.1 |
| 2014/0374294 A1 | * | 12/2014 | Joyce | A61B 50/36 206/363 |

* cited by examiner

*Primary Examiner* — Dana Ross
*Assistant Examiner* — Joe E Mills, Jr.
(74) *Attorney, Agent, or Firm* — Sughrue Mion, PLLC

(57) ABSTRACT

An apparatus for the destruction of needles and other sharp objects using electrical current. In addition to an incineration ports where needles are inserted for destruction, the apparatus also includes certain improvements related to the shape and composition of the electrical contacts, certain safety circuits related to power source overheating, and digital monitoring and control of current throughput to minimize sparking.

31 Claims, 10 Drawing Sheets

Waveform in Figure 8 after Smoothing with Capacitor

APPARATUS FOR DESTROYING SHARP OBJECTS AND METHOD OF USE

RELATED APPLICATIONS

This application claims priority to U.S. Provisional Application No. 62/869,390 filed Jul. 1, 2019 and U.S. Provisional Application No. 62/942,041 filed Nov. 29, 2019. The entire contents of the above applications are hereby incorporated by reference as though fully set forth herein.

FIELD

The present invention relates in general to devices designed for the destruction of sharp objects. More specifically, the present invention relates to devices designed destroy needles and other sharp objects in the medical field.

BACKGROUND

Needles and other sharp objects are ubiquitous in the medical field providing a range of uses from performing surgical procedures to administering drugs and other therapies to patients. However, since these tools are used for primarily for invasive procedures, safety protocols dictate that these tools must be properly disposed of in order to prevent cross-contamination and minimize the spread of bacteria from patient to patient. One way of disposing of needles to ensure they are no longer used is to destroy the tip of the needle after it has come in contact with a patient. Devices for destroying needles are known in the art and typically include a lead acid battery connected to silver cadmium contacts with a recharging circuit where the power supplied to the contacts is sufficient to either ablate or melt the needle. Power delivery is generally handled by one of two methods: the arc ablation or melting method. The arc method uses very high voltage at low currents, and conversely, the melting method uses low voltage at very high currents. In either method, the physics are constant. Power (voltage×current) must be delivered in a high enough quantity in a short enough time period that the steel of the needle or sharp object cannot withstand it. The arc (high voltage) method creates a more consistent burn and does not create as much heat in the system (it is more efficient), but due to the nature of its high voltage, it is inherently more dangerous and requires more safety interlocks to disable the unit if the enclosure is opened in any way. Currently, these interlocks are all analog physical interlocks. The melting method uses a very low voltage (4 volts), but high current. Because of the nature of working with low voltage, this method is inherently safer and less dangerous.

However, conventional needle destruction devices employing the melting method lack necessary safety mechanism to prevent surges in current from destroying the device. For example, as the needle melts, a ball of molten steel is produced between the contacts. This material remains until either: the ball grows so large that it falls through the space between the contacts, or the user twists the needle to break the surface tension of the molten slag. If this slag accumulates to the point of wrapping underneath the silver plate and touches the bronze beneath the silver plates, a weld is created that causes a permanent connection between them. This permanent connection causes very high current to flow for a prolonged amount of time—if the connection is not shut off, the batteries will vent their electrolyte material, rendering the system useless.

Accordingly, there is a need for an improved needle destruction device capable of monitoring system parameters and providing safeguards to prevent current surges to the device being destroyed.

BRIEF SUMMARY OF THE INVENTION

It is the object of the present invention to provide an improved device for destroying needles and sharp objects through the inclusion of an integrated monitoring system that is operable to monitor various system parameters and determine proper current adjustments to the incineration ports of the device.

One embodiment of the device includes an incineration port having two opposing electrodes each having an electrically conductive contact, a power source operable to power the electrodes, a plurality of system sensors operable to monitor current, temperature, voltage, and usage information, and a microcontroller unit (MCU) having a processor that is operable to communicate with the various system sensors and interface with the power source and electrode to regulate current being delivered to the electrode.

In an alternative embodiment, the geometry of the electrodes are configured to maximize efficiency.

In yet another embodiment, and in order to provide additional safeguards, the device includes an operational amplifier in communication with the power source for the system, wherein the operational amplifier is operable to monitor the temperature of the battery in order to protect it from damage or other malfunction if the safety mechanisms provided by the microcontroller unit (MCU) fail. For this embodiment, the operational amplifier has built in hysteresis that allows it only to be triggered at critical high temperatures, but it does not re-enable until a pre-set drop in temperature has been achieved.

In yet another embodiment, the device includes an integrated disposal container that is positioned directly under the electrodes for easy disposal of destroyed needles and is capable of being removed. The container may also include an integrated locking mechanism for holding the container in place, as well as a spring-loaded door to automatically close the container when it is being removed from the device for disposal, protecting users from spilling the contents of the container.

In other embodiments, the device includes a syringe guide operable to contain excess sparks and shield the user. As a further option, the device can include a fan that pulls fumes through a carbon fiber element.

DETAILED DESCRIPTION

Figure 1:
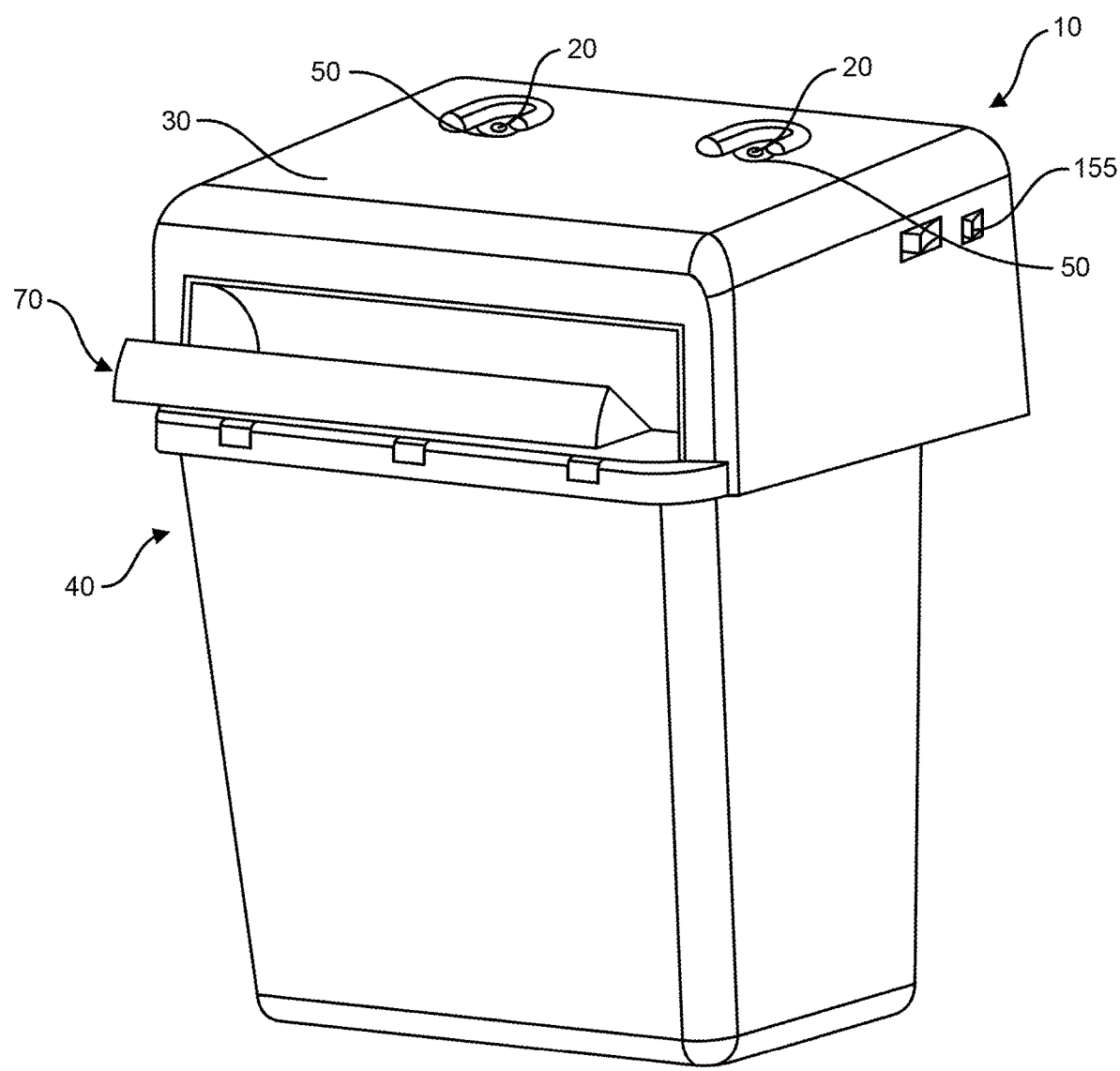
FIG. 1 is a perspective view of the device attached to the disposal container.
Figure 2:
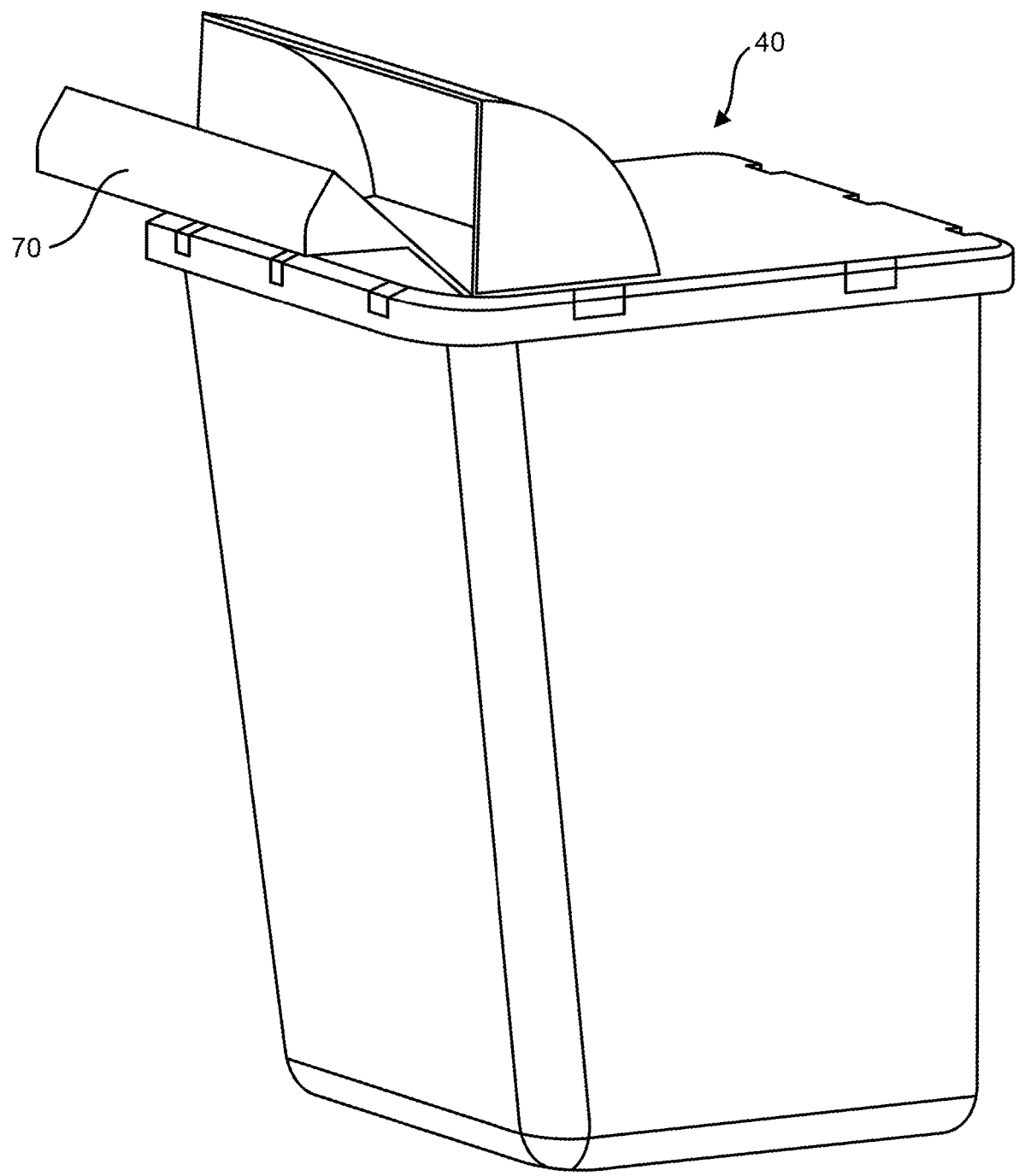
FIG. 2 is a perspective view of the disposal container.

Turning to FIGS. 1-2, a first embodiment of the device for destroying needles or other sharp objects is shown. The device shown includes a top housing 10 having at least one incineration port 20 disposed on the outer surface 30 of the housing 10 with the top housing 10 being attached to a disposal container 40 that is removably attached to the top housing 10. As shown in FIG. 1, more than one incineration port 20 can be used to accommodate needles or other sharp objects of different sizes. The incineration ports 20 each include an aperture 50 in the top housing 10 that provides access to the electrodes 105, 110 (as shown in FIG. 3).

FIG. 2 shows the disposal container 40 after it has been removed from the top housing 10. Preferably, the disposal container 40 is positioned directly beneath the incineration ports 20 as a convenient location for the user to dispose of blunt syringes as well as intact needles should the user not wish to destroy the sharp object. The sharps container has an integrated locking mechanism (not shown) which firmly holds the container into the correct attached position in the device, as well as a spring-loaded door 70 to automatically close the disposal container 40 when it is removed from the system, protecting users from spilling the contents of the container.

Figure 3:
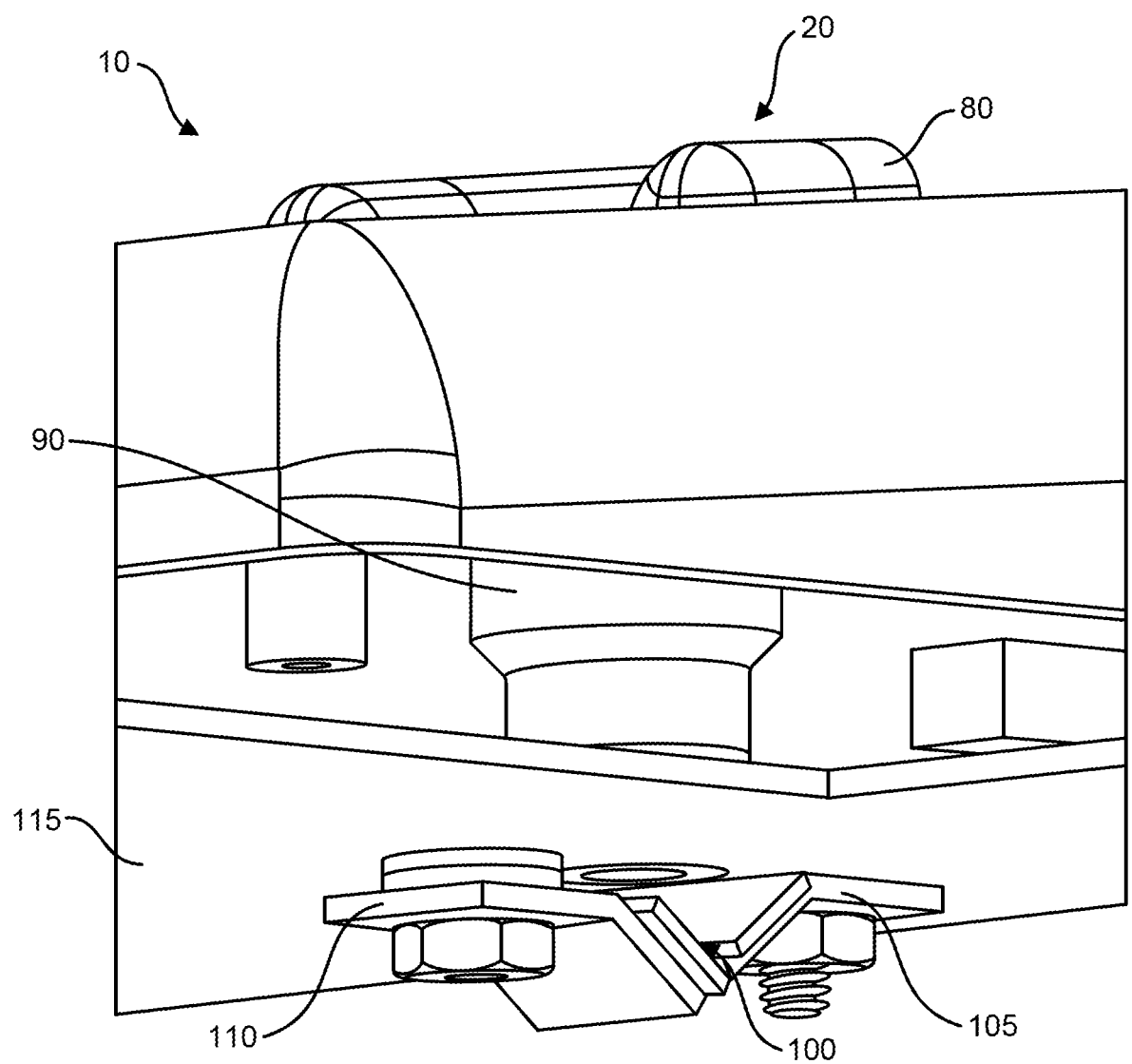
FIG. 3 is a perspective view of the incineration port showing the syringe guide within the housing.

Turning to FIG. 3, each incineration port 20 may further include a syringe guide 70. The syringe guide 70 includes a recessed barrier 80 surrounding the aperture 50 at the top surface 30 of the housing 10 as well as a guiding tube 90 to guide the sharp object upon insertion into the device to the contact point 100 between the first electrode 105 and second electrode 110. The electrodes 100, 105 are attached to a circuit board 115, which may be a printed circuit board (PCB).

Figure 4:
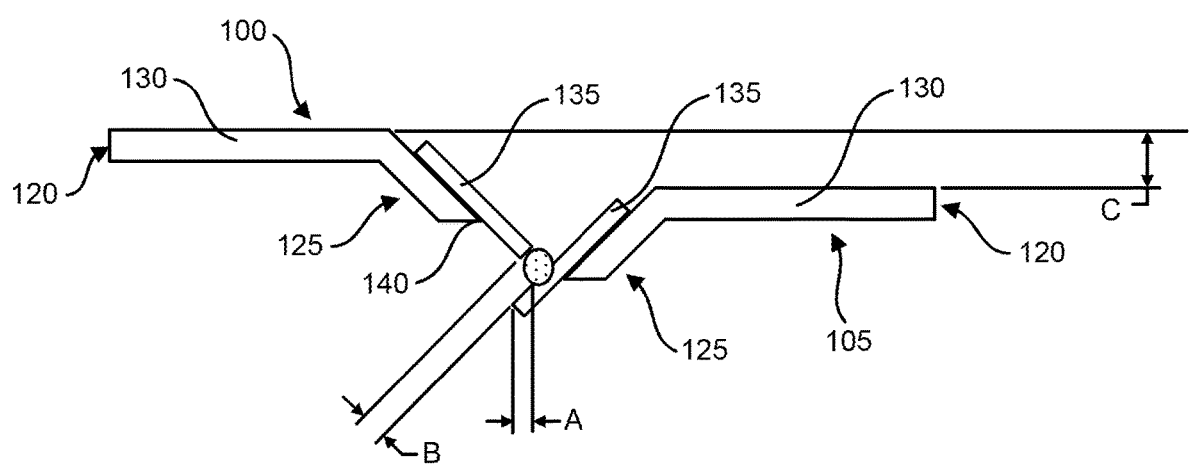
FIG. 4 is a profile view of the incineration port showing the electrodes
Figure 5A:
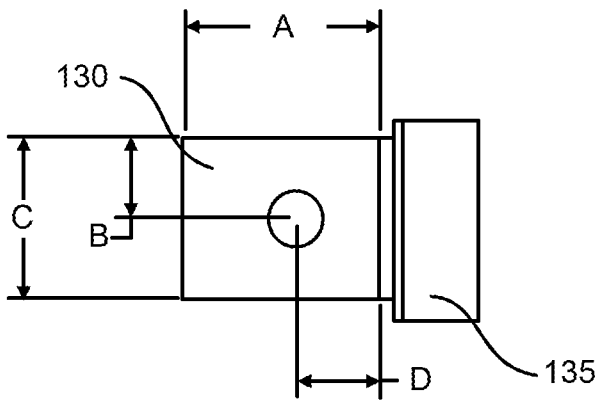
FIG. 5A is a top view of an electrode.
Figure 5B:
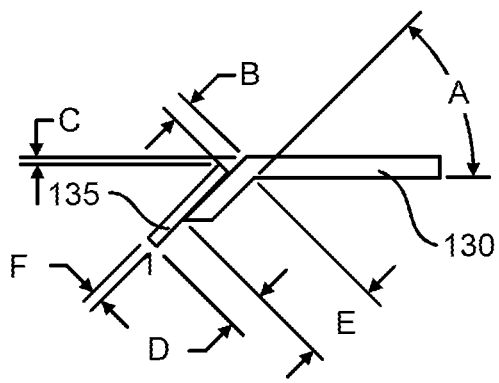
FIG. 5B is a side view of an electrode.
Figure 5C:
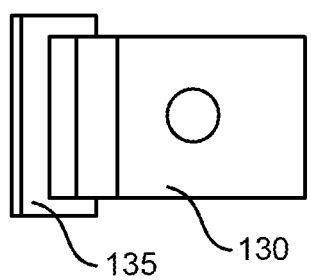
FIG. 5C is a bottom view of an electrode.

Turning to FIG. 4, the preferred configuration of each electrode 100, 105 is shown. Each incineration port 20 includes a first electrode 100 and an opposite facing second electrode 105, which are made from materials capable of conducting electricity. For the preferred embodiment as shown in FIG. 4, each electrode includes a flat portion 120 and an angled portion 125 that make up a base 130 attached to a contact 135, with the angled portion 125 being bent downward at an offset angle. A from the horizontal plane of the flat portion 120. Although any electrically conductive materials can be used, it is preferred that the base 130 of each electrode be made of phosphor bronze and the contact 135 be made of silver or a silver alloy. The preferred configuration of the electrodes is shown in FIG. 4 and FIGS. 5A-C. The configuration depicts the flat portion 120 of the second electrode 105 being vertically offset from the flat portion 120 of the first electrode 100 with the contact 135 extending beyond the terminal end 140 of the base 130 and the offset angle A for each electrode being 45° (as seen in FIG. 5B). Turning to FIG. 4, the dimensions between contacts 135 are shown, with the preferred length for A being 1.06 mm and the preferred length for B being 1.46 mm. FIG. 5A depicts a top view of the exemplary embodiment of the electrode, with length A being 15.4 mm, length B being 6.35 mm, length C being 12.7 mm, and length D being 6.5 mm. FIG. 5B depicts a side view of the electrode, with the following preferred dimensions: B as 1.8 mm, C as 0.57 mm, D as 3.1 mm, E as 6.23 mm, and F as 1 mm. In another embodiment, the angled portions 125 of each electrode 100, 105 has a contact 135 with an overhang length (depicted by D in FIG. 5B) of 2-3 mm. The configuration as described substantially reduces the likelihood of any slag accumulation becoming welded to the bronze portion of the electrode.

Turning to FIG. 6, each electrode 100, 105 is powered by a power source and may be hard wired or integrated into a printer circuit board (PCB) attached to the interior of the top housing 10. For the preferred embodiment, these electrodes are powered by up to three or more separate batteries arranged in a parallel configuration. Although not required, it is preferred that the batteries used be 18650-size lithium-ion batteries, or other similar Lithium manganese nickel/INR batteries, with nickel strips spot welded to the terminals for maximum current transfer; these strips are then soldered to the circuit board or PCB. Optionally, in an effort to monitor temperature of the batteries, each battery can further include a temperature monitor sensor that is thermally bonded to the battery. Other sensors can be deployed within the device, including a current sensor 150 operable to detect current being delivered from the power source 145 to the electrode 100, 105.

Optionally, another embodiment of the system includes a microcontroller unit (MCU) 155 with an integrated processor configured to interface and communicate with the power source, electrodes, and system sensors. A preferred version of the MCU 155 is the STMicroelectronics 32-bit microcontroller unit. This MCU 155 is capable of running at 20 MHz and offers 256 KB of program space with 64 KB of RAM. The MCU 155 may further include a standard USB connection 155 disposed on the outer surface 30 of the top housing 10 (as shown in FIG. 1). The USB connection 155 provides communication means between the MCU 155 and a separate computing device (not shown), with command line interface for operating the system if desired. The USB connection 155 also charges the power source 145 with the 5V USB bus voltage and allows for easy updating of MCU firmware via specialized command set.

An exemplary embodiment of the present invention includes a feedback loop monitoring the electrical current and/or power delivered to the sharp implement in real time and modifying the rate of power delivered to electrodes 100, 105 to a level where detectable sparks are reduced or eliminated, while simultaneously destroying the sharp implement. More specifically, in existing sharps destruction implementations, full power is applied to the sharp implement immediately and instantaneously upon insertion into the destruction device. This often results in large spikes of current as pieces of the sharp are destroyed, which can cause visibly apparent sparks. By implementing a Managed Power Spark Abatement system into a sharps destruction device, the power can be slowly ramped into the needle to achieve the most efficient destruction with minimal sparking.

To achieve the spark abatement, the system constantly monitors the current delivered to the sharp in real time. As shown in FIG. 6, the MCU is operable to continuously monitor the current consumption at the electrodes 100, 105 by way of current signals 160 communicated to the MCU 155 by the current sensor 150. A small amount of power is initially applied; once the destruction process has begun, the power is ramped to a level that allows destruction of the sharp at the maximum rate that does not produce sparks. Once current is no longer detected, the power is again reduced to the initial level in anticipation of a new destruction event.

In one embodiment, the maximum value of power allowed is the full power of the system, but the rate of ramping to that full power from a minimum power of about 10% is controlled and ramped upward slowly to prevent spark creation by the sudden inrush of current. The rates of ramping are completely configurable and are typically adjusted upward 1-2% at a time every 10 ms interval. If at any time the needle loses connection with the burning contacts, or becomes oxidized causing high resistance, the system will detect the fall in electrical current and immediately bring down the applied power to a lower value and begin monitoring for the needle to resume destruction.

Figure 6A:
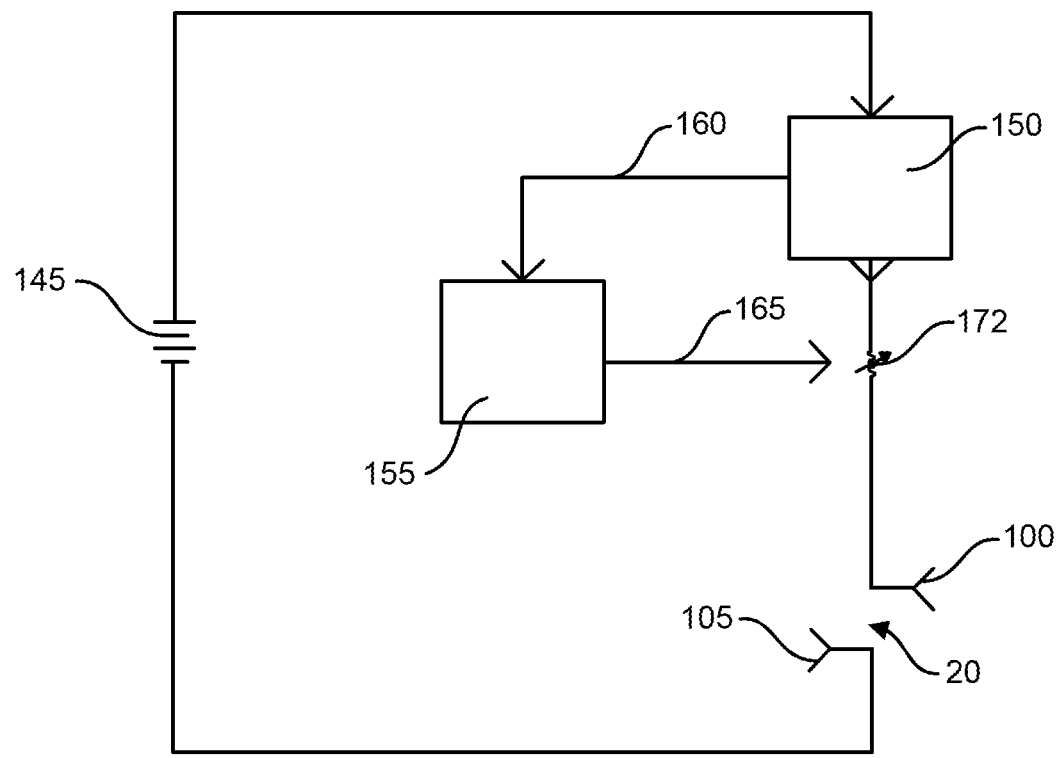
FIG. 6A is a system diagram.
Figure 8:
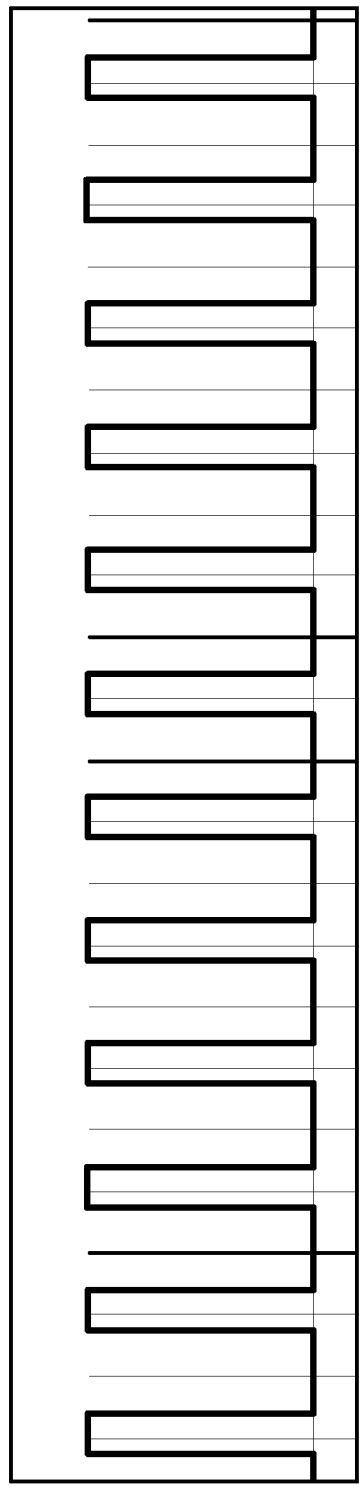
FIG. 8 is an exemplary PWM signal.
Figure 9:
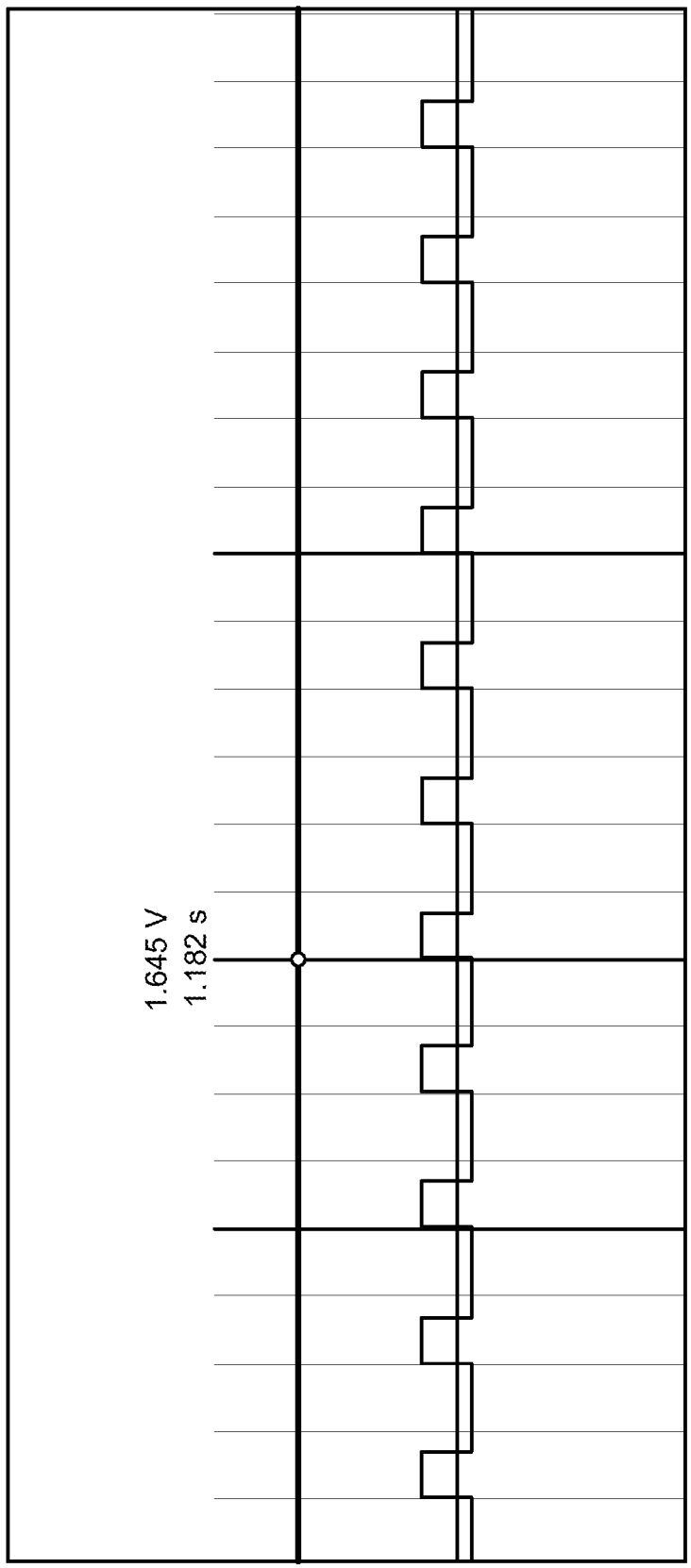
FIG. 9 is another exemplary PWM signal.

Many methods could be used to achieve the varied power levels required for spark abatement. Two such methods include analog biasing of an external bipolar-junction transistor (BJT) and pulse-width modulated (PWM) metal-oxide semiconductor field-effect transistor (MOSFET) switching. The first method uses a BJT as a variable resistor to limit the power rate delivered to the sharp slowly to the desired level. This desired level is typically the full power of the system but could be some lower level if only smaller needles are to be destroyed. This transistor would be driven by a smoothed PWM signal as seen in FIG. 9. The second method pulses full power to the sharp many times per second at a variable duty cycle to achieve the desired average power delivery. This transistor would be driven directly with a PWM signal as seen in FIG. 8. The basic equivalent of both methods is a variable resistance 172 as seen in FIG. 6A. In either embodiment, variable resistance element 172 is controlled by MCU 155 via control signal 165.

Various power levels are required depending on the length and gauge of the needle. For example, the power required to destroy to a 30-gauge needle without sparks may not be able to destroy a 21-gauge needle, while the power required to destroy a 21-gauge needle without sparks may cause significant visible sparking when applied to a 30-gauge needle. In order to mitigate this effect, the system can infer needle gauge from the current draw present during the initial low-power sensing phase. The amount of power applied during the high-power destruction phase is then managed according to this inferred needle gauge to produce optimum destruction without visible sparking. Currently, a full correlation between needle size and current draw can only be seen in post processing of the data, but we speculate that, with improvements in applied computer processing power, this could be accomplished in real time and further refinements to the maximum power delivered could be made. This could be accomplished by using either discrete analog components (such as operational amplifiers) or with a digital circuit that is programmable (microcontroller, embedded PC, etc.). A digital circuit could also feature a method of logging the delivered power to each needle for later analysis and adjustment.

The PWM can be accomplished in several ways, but typically would be accomplished using a dedicated PWM timer circuit found within many microcontrollers. These microcontrollers have dedicated timers that can be configured to output a PWM pulse with a desired frequency and pulse width. The frequency and/or pulse width can be modified during the time of needle destruction to manage the power delivery as described via a feedback software loop. Once set, the timers count the configured "on time" and then turn the PWM output off, then count the configured "off time" and turn the PWM output back on. This would typically happen thousands of times per second (i.e. on the order of kilohertz).

Through the instantaneous measurement of current delivered to the needle, and a comparison of the currently used PWM settings, needle gauge size may be determined. At any given PWM rate, larger needles will draw more power than smaller needles, as their electrical resistance is lower. Once the determination that a larger needle is present is made, additional power can be delivered to those larger needles requiring such, while smaller gauge needles may continue to use smaller amounts of current reducing spark risk.

The control algorithm is based on current draw, and duty cycle applied. The system starts by applying a non-constant duty cycle (typically 10%) and monitors for any current draw. If no current is detected, the system stays at the low duty cycle and simply waits for a user to insert a needle for destruction. Once current is detected, the system begins to increase the PWM (and thereby the power delivered) at a rate typically 1-2% per sampling cycle. Each cycle is approximately 10 ms. Therefore, in approximately 1 second or less, if the needle is in constant contact with the power delivery contacts, the system is delivering full power to the needle currently being destroyed. If, during a burn cycle, the current detected drops off, the system reduces power immediately by some amount (typically 20%) each 10 ms cycle to reduce the chances of spark when the needle re-engages the contacts. Increasing the PWM % is then resumed once current is detected again. In this way, a sudden inrush of current is limited, and spark creation is minimized.

As an additional safeguard to protect the power source from damage, fire, or other malfunction, the device may include a back-up additional hardware safety circuit equipped with an operational amplifier operable to monitor the temperatures of the power source 145. Because the op-amp does not use software, it adds additional protections to the power source 145 in the unlikely event of the MCU 155 failing. In practice, the operational amplifier will be set to disable the power source 145 at a higher temperature than what is required for the MCU 155 to disable the power source 145. Additionally, this operational amplifier circuit has built in hysteresis in the same way that the software does; in other words, the operational amplifier triggers at a high temperature, but does not re-enable until 10 degrees below that has been achieved. This prevents the device from rapidly switching on and off as the temperature floats right around the shut off temperature. Without this temperature monitoring, during a critical fault, the power source 145, in the case of a battery, would either vent their electrolyte, or some point within the system would melt solder in unpredictable ways with unpredictable results and unit damage.

Figure 7:
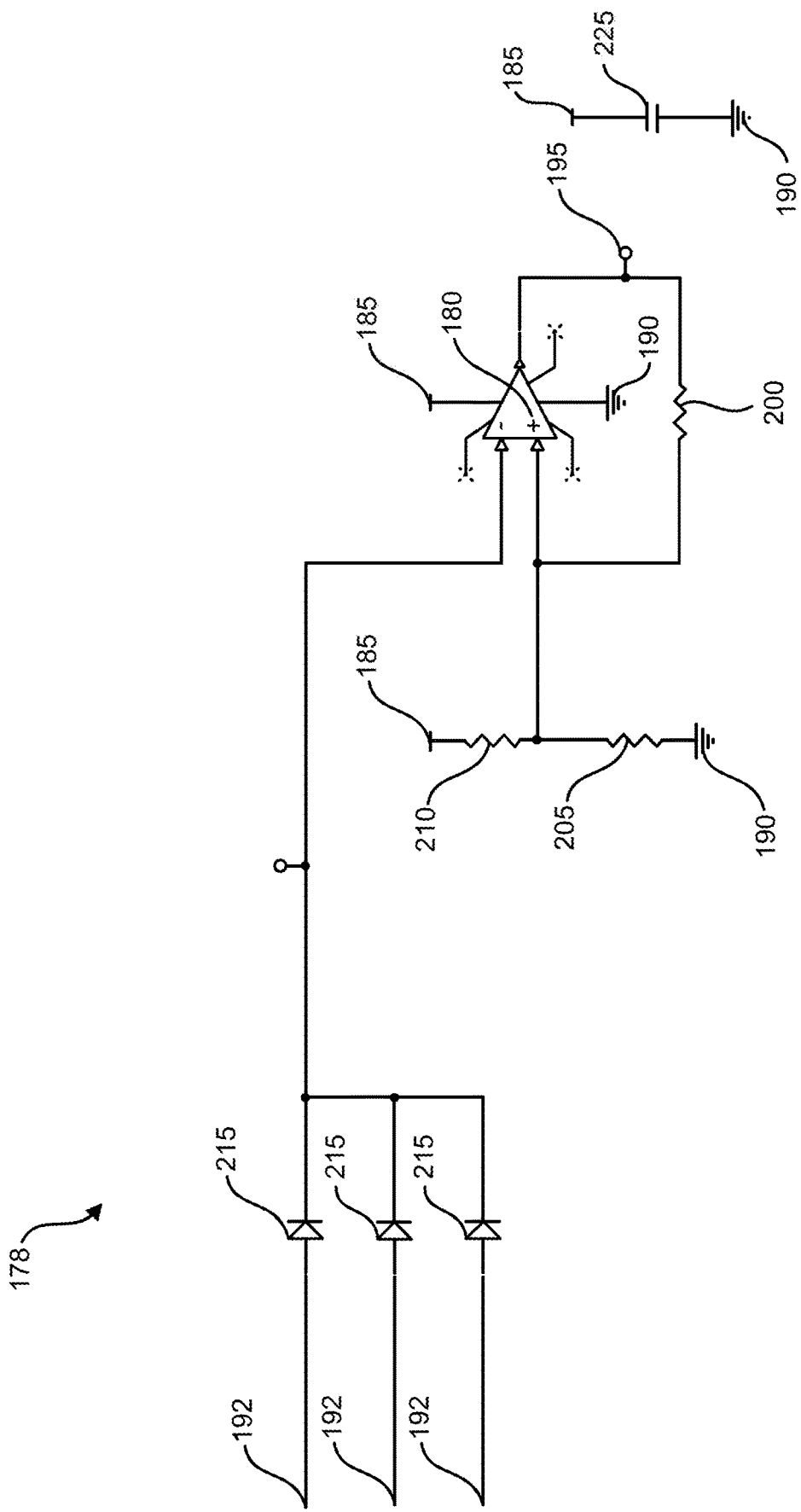
FIG. 7 is a circuit diagram of an exemplary temperature safety circuit.

Turning to FIG. 7, exemplary embodiment of the hardware safety circuit 178 is shown. The hardware safety circuit includes an operational amplifier 180 with the negative power supply 190 going to ground and its positive power supply node 185 being powered by an individual power source, such as a 3V3 battery. This power supply node 185 is connected to the ground 190 and a capacitor 225 with a capacitance of 0.10 μF. The current received at the inverting input signal of the operational amplifier 180 is originates from three separate temperature sensors 102, such as the ADCI 7 B1 TempSense, each attached to three separate power sources 145 (not shown), before passing through individual corresponding diodes 215. The current received at the non-inverting input signal of the operational amplifier 180 is received from a node 185 consisting of a power source, such as a 3V3 battery and a 7.5 kiloohm resistor 210, as well as a grounding circuit 190 with a 3.3 kiloohm resistor 205. The amplified output from the operational amplifier 180 passes through a safety 195 and a 33 kiloohm resistor 200.

Figure 6B:
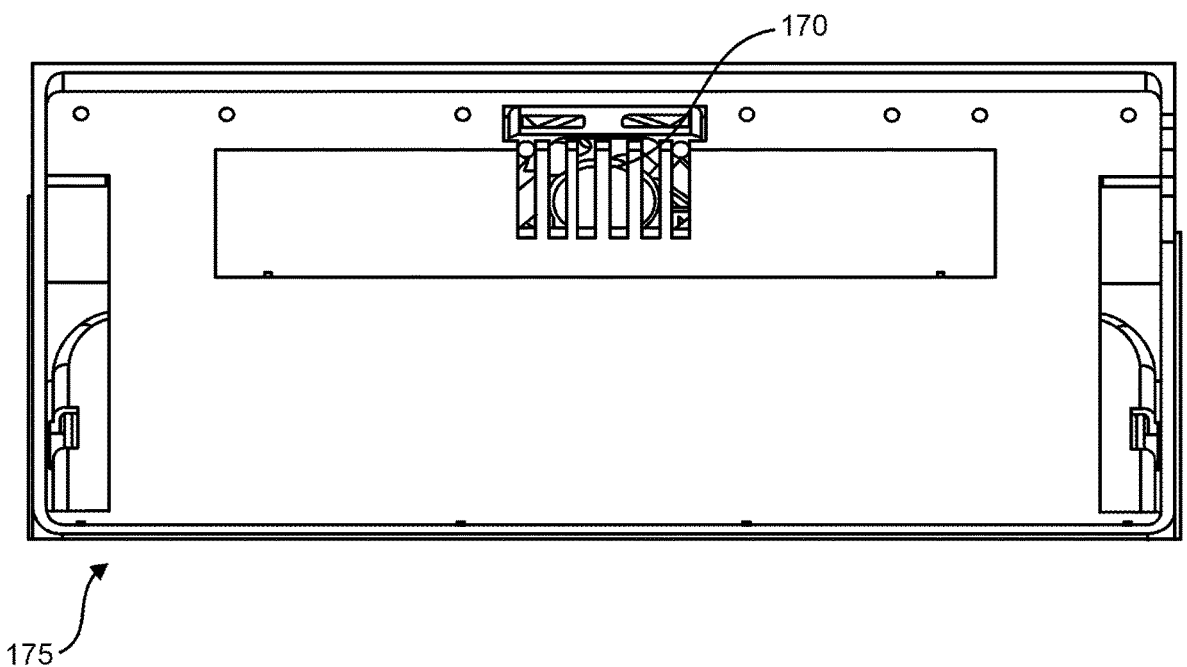
FIG. 6B is a bottom view of the sharps destruction unit.

Turning to FIG. 6B, the device may also include a fan 170 disposed at the base 175 of the device that is operable to pull any fumes through a carbon filter element (not shown).

For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the method (and components of the individual operating components of the method) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections might be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. An apparatus for destroying needles and sharp objects comprising:
    an incineration port, the incineration port comprising a plurality of electrodes, wherein the plurality of electrodes are operable to receive a needle or other sharp object;
    a power source, wherein the power source is in communication with the incineration port and wherein the power source is operable to provide electrical power to each electrode of the plurality of electrodes;
    a plurality of sensors comprising a current sensor;
    a processor, wherein the processor is operable to communicate with the plurality of sensors, and wherein the processor is operable to interface with the power source and the plurality of electrodes; and
    a transistor,
    wherein each electrode of the plurality of electrodes comprises a flat portion and an angled portion, each angled portion comprises a contact and a base, and each contact and each base comprises a terminal end,
    wherein each angled portion of each electrode is bent downward at an offset angle from a horizontal plane of the flat portion of the electrode,
    wherein, for each angled portion, a portion of the contact of the angled portion extends beyond the terminal end of the base of the angled portion and defines an overhang length,
    wherein the current sensor is in communication with the processor, and the current sensor is operable to detect current being delivered to the plurality of electrodes by the power source, and
    wherein the processor is operable to infer a size of the needle or other sharp object inserted into the incineration port based on an output of the current sensor, to drive the transistor using a pulse-width modulated signal, and to modify the pulse-width modulated signal based on the inferred size of the needle or other sharp object, thereby controlling a flow of power from the power source to the plurality of electrodes in a manner that minimizes sparking.

2. The apparatus of claim 1, wherein the offset angle for each electrode of the plurality of electrodes is 45°.

3. The apparatus of claim 1, wherein the overhang length of each electrode of the plurality of electrodes is 2-3 mm.

4. The apparatus of claim 1, wherein the base of each electrode of the plurality of electrodes is made from phosphor bronze.

5. The apparatus of claim 1, wherein the contact of each electrode of the plurality of electrodes is made from silver or a silver alloy.

6. The apparatus of claim 1, further comprising a USB port operable to communicate with the processor.

7. The apparatus of claim 1, further comprising a safety circuit, the safety circuit being operable to monitor a temperature of the power source and to disable the power source at a threshold temperature.

8. The apparatus of claim 1, further comprising an integrated disposal container.

9. The apparatus of claim 1, wherein the incineration port comprises a syringe guide.

10. An apparatus for destroying needles and sharp objects comprising:
    an incineration port, said incineration port comprising a first electrode and a second electrode, wherein the first electrode and the second electrode are operable to receive a needle or a sharp object;
    a power source in communication with said incineration port, wherein the power source is operable to provide electrical power to the first electrode and the second electrode;
    a plurality of sensors comprising a current sensor;
    a microcontroller unit comprising a processor, wherein the microcontroller unit is in communication with the plurality of sensors, and wherein the processor is operable to interface with the power source, the first electrode, and the second electrode; and
    a transistor,
    wherein the current sensor is in communication with the microcontroller unit, and the current sensor is operable to detect current being delivered to the first electrode and the second electrode by the power source, and
    wherein the microcontroller unit is operable to: infer a size of the needle or the sharp object inserted into the incineration port based on an output of the current sensor, to drive the transistor using a pulse-width modulated signal, and to modify the pulse-width modulated signal based on the inferred size of the needle or the sharp object, thereby controlling a flow of power from the power source to the first electrode and the second electrode in a manner that minimizes sparking.

11. The apparatus of claim 10, wherein each of the first electrode and the second electrode comprises a flat portion and an angled portion, wherein each angled portion comprises a contact attached to a base, wherein the contact and the base each have a terminal end, wherein the angled portion of the first electrode and the second electrode is bent at an offset angle from a horizontal plane of the flat portion, wherein a portion of the contact extends beyond the terminal end of the base and defines an overhang length.

12. The apparatus of claim 11, wherein the offset angle for each of the first electrode and the second electrode is 45°.

13. The apparatus of claim 11, wherein the overhang length of the first electrode and the second electrode is 2-3 mm.

14. The apparatus of claim 11, wherein the base of each of the first electrode and the second electrode is made from phosphor bronze.

15. The apparatus of claim 11, wherein the contact of each of the first electrode and the second electrode is made from silver or a silver alloy.

16. The apparatus of claim 10, further comprising a USB port operable to communicate with the microcontroller unit.

17. The apparatus of claim 10, further comprising a safety circuit, wherein the safety circuit is operable to monitor a temperature of the power source and to disable the power source at a threshold temperature.

18. The apparatus of claim 10, further comprising an integrated disposal container.

19. The apparatus of claim 10, wherein the incineration port comprises a syringe guide.

20. An apparatus for destroying needles and sharp objects comprising:
an incineration port comprising a first electrode and a second electrode, wherein the first electrode and the second electrode are operable to receive a needle or a sharp object;
a power source in communication with the incineration port and operable to provide electrical power to the first electrode and the second electrode;
a current sensor operable to detect current being delivered from the power source to the first electrode and the second electrode;
a variable resistance element operable to regulate an amount of current being delivered to the first electrode and the second electrode; and
a microcontroller unit comprising a processor that is in communication with the current sensor and the variable resistance element,
wherein the processor is operable to interface with the power source, the first electrode, and the second electrode,
wherein both the current sensor and the variable resistance element are in communication with the microcontroller unit,
wherein the processor of the microcontroller unit is configured to receive data from the current sensor and determine if a current adjustment is required, and
wherein, based on determining that the current adjustment is required, the processor is configured to compute the required current adjustment and send a signal to the variable resistance element which will result in a modification of the amount of current passing to the first electrode and the second electrode.

21. The apparatus of claim 20, further comprising a transistor, wherein the microcontroller unit is operable to: infer a size of the needle or the sharp object inserted into the incineration port based on an output of the current sensor, to drive the transistor using a pulse-width modulated signal, and to modify the pulse-width modulated signal based on the inferred size of the needle or the sharp object, thereby controlling a flow of power from the power source to the first electrode and the second electrode in a manner that minimizes sparking.

22. The apparatus of claim 20, wherein each of the first electrode and the second electrode has a flat portion and an angled portion, wherein each angled portion comprises a contact attached to a base, wherein each contact and each base comprise a terminal end, wherein the angled portion of each of the first electrode and the second electrode is bent downward at an offset angle from a horizontal plane of the flat portion, and wherein a portion of each contact extends beyond the terminal end of the base and defines an overhang length.

23. The apparatus of claim 22, wherein the offset angle for each of the first electrode and the second electrode is 45°.

24. The apparatus of claim 22, wherein the overhang length of each of the first electrode and the second electrode is 2-3 mm.

25. The apparatus of claim 22, wherein the base of each of the first electrode and the second electrode is made from phosphor bronze.

26. The apparatus of claim 22, wherein the contact of each of the first electrode and the second electrode is made from silver or a silver alloy.

27. The apparatus of claim 20, further comprising a USB port operable to communicate with the microcontroller unit.

28. The apparatus of claim 20, further comprising a safety circuit, wherein the safety circuit is operable to monitor a temperature of the power source and to disable the power source at a threshold temperature.

29. The apparatus of claim 20, further comprising an integrated disposal container.

30. The apparatus of claim 20, wherein the incineration port comprises a syringe guide.

31. An apparatus for destroying needles and sharp objects comprising:
an incineration port, the incineration port comprising a plurality of electrodes, wherein the plurality of electrodes are operable to receive a needle or other sharp object;
a power source, wherein the power source is in communication with the incineration port and wherein the power source is operable to provide electrical power to each electrode of the plurality of electrodes;
a plurality of sensors comprising a current sensor;
a processor, wherein the processor is operable to communicate with the plurality of sensors, and wherein the processor is operable to interface with the power source and the plurality of electrodes; and
a variable resistance element,
wherein each electrode of the plurality of electrodes comprises a flat portion and an angled portion, each angled portion comprises a contact and a base, and each contact and each base comprise a terminal end,
wherein each angled portion of each electrode is bent downward at an offset angle from a horizontal plane of the flat portion of the electrode,
wherein, for each angled portion, a portion of the contact of the angled portion extends beyond the terminal end of the base of the angled portion and defines an overhang length,
wherein the processor is a microcontroller,
wherein the current sensor is operable to detect current being delivered to the plurality of electrodes by the power source, and the variable resistance element is operable to regulate an amount of current being delivered to the plurality of electrodes,
wherein the current sensor and the variable resistance element are in communication with the processor, and
wherein the microcontroller is operable to: receive data from the current sensor; determine whether an adjustment in the amount of current delivered to the plurality of electrodes is required; when it is determined that an adjustment in the amount of current delivered to the plurality of electrodes is required, compute the required adjustment; and provide a signal to the variable resistance element wherein the signal results in a modification of the amount of current passing to the plurality of electrodes.

\* \* \* \* \*